US007462463B1

(12) United States Patent
Tirrell

(10) Patent No.: US 7,462,463 B1
(45) Date of Patent: Dec. 9, 2008

(54) FUSION PROTEIN MICROARRAYS AND METHODS OF USE

(75) Inventor: David A. Tirrell, Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 388 days.

(21) Appl. No.: 10/015,956

(22) Filed: Dec. 10, 2001

Related U.S. Application Data

(60) Provisional application No. 60/254,516, filed on Dec. 8, 2000.

(51) Int. Cl.
*G01N 33/35* (2006.01)
(52) U.S. Cl. .......................................... 435/7.9; 530/350
(58) Field of Classification Search ................. 435/7.9; 530/350
See application file for complete search history.

(56) References Cited

U.S. PATENT DOCUMENTS 5,641,648 A * 6/1997 Ferrari et al. ............... 435/69.1
6,090,911 A * 7/2000 Petka et al. .................. 530/300

OTHER PUBLICATIONS

Afanassiev, et al., "Preparation of DNA and Protein Micro-Arrays on Glass Slides Coated with an Agarose Film", *Nucl. Acid Res.* 28(12):1-5 (2000).
Arenkov, et al., "Protein Microchips: Use for Immunoassay and Enzymatic Reactions," *Anal. Biochem.* 278:123-131 (2000).
Ge, Hui, "UPA, a Universal Protein Array System for Quantitative Detection of Protein-Protein, Protein-DNA, Protein-RNA and Protein-Ligand Interactions", *Nuc. Acid. Res.* 28(2):1-7 (2000).
Kricka, et al., "Multispot Array Technologies", *Encl. of Life Sci.* 1-8, (2001).
MacBeath, et al., "Printing Proteins as Microarrays for High-Throughput Function Determination", *Sci.* 289:1760-1763 (Sep. 2000).
Sadowski, Ivan, "Protein Domain Fusion", *Encl. of Life Sci.* 1-7, (2001).
Caldwell, S., et al., "Limits of diffusion in the hydrolysis of substrates by the phosphotriesterase from *Pseudomonas diminuta*," *Biochemistry*, 30(30):7438-44, Jul. 30, 1991.
Drmanac, R., et al., "cDNA screening by array hybridization," *Methods Enzymol.*, 303:165-78, 1999.
Ekins, R., et al., "Multianalyte microspot immunoassay—microanalytical "compact disk" of the future," *Clin Chem.*, 37(11):1955-67, Nov. 1991.
Hentz, N., et al., "Bifunctional fusion proteins of calmodulin and protein A as affinity ligands in protein purification and in the study of protein-protein interactions," *Anal Chem.*, 68(22):3939-44, Nov. 15, 1996.

(Continued)

*Primary Examiner*—Karen Cochrane Carlson
*Assistant Examiner*—Agnes B. Rooke
(74) *Attorney, Agent, or Firm*—Seed IP Law Group PLLC

(57) ABSTRACT

The present invention provides a microarray having one or more fusion proteins non-covalently attached to a solid support. Non-covalent attachment is achieved by designing a fusion protein having a polyanionic domain attached to a subject protein, and attaching the fusion protein to a solid support having a polycationic coating.

9 Claims, 2 Drawing Sheets

OTHER PUBLICATIONS

Khrapko, K., et al., "A method for DNA sequencing by hybridization with oligonucleotide matrix," *DNA Seq.*, 1(6):375-88, 1991.

Krejchi, M., et al., "Chemical sequence control of beta-sheet assembly in macromolecular crystals of periodic polypeptides," *Science*, 265(5177):1427-32, Sep. 2, 1994.

Lemmo, A., et al., "Inkjet dispensing technology: applications in drug discovery," *Curr Opin Biotechnol.*, 9(6):615-7, Dec. 1998.

Ljungquist, C., et al., "Immobilization and affinity purification of recombinant proteins using histidine peptide fusions," *Eur J Biochem.*, 186(3):563-9, Dec. 22, 1989.

Matson, R., et al., "Biopolymer synthesis on polypropylene supports. I. Oligonucleotides," *Anal Biochem.*, 217(2):306-10, Mar. 1994.

Messing, R., ed., *Immobilized Enymes for Industrial Reactors*, Academic Press, New York, 1975, Ch. 5, "Immobilization by Adsorption and Inorganic Bridge Formation," pp. 79-98.

McGrath, K., et al., "Genetically directed syntheses of new polymeric materials, expression of artificial genes encoding proteins with repeating -(AlaGly)$_3$ProGluGly- elements," *J. Am. Chem. Soc.*, 114:727-733, 1992.

Mulbry, W., et al., "Parathion hydrolase specified by the Flavobacterium opd gene: relationship between the gene and protein," *J Bacteriol.*, 171(12):6740-6, Dec. 1989.

Okamoto, T., et al., "Microarray fabrication with covalent attachment of DNA using bubble jet technology," *Nat Biotechnol.*, 18(4):438-41, Apr. 2000.

Omburo, G., et al., "Characterization of the zinc binding site of bacterial phosphotriesterase," *J Biol Chem.* 267(19):13278-83, Jul. 5, 1992.

Ong, E., et al., "Enzyme immobilization using the cellulose-binding domain of a *Cellulomonas fimi* exoglucanase," Bio/technology, 7:604-607, 1989.

Piesecki, S., et al., "Immobilization of β-Galactosidase for application in organic chemistry using a chelating peptide," *Biotechnology and Bioengineering*, 42:178-184, 1993.

Sassenfeld, H., "Engineering proteins for purification," *Trends Biotechnol.*, 8(4):88-93, Apr. 1990.

Schena, M., et al., "Quantitative monitoring of gene expression patterns with a complementary DNA microarray," *Science*, 270(5235):467-70, Oct. 20, 1995.

Stempfer, G., et al., "A fusion protein designed for noncovalent immobilization: stability, enzymatic activity, and use in an enzyme reactor," *Nat Biotechnol.*, 14(4):481-4, Apr. 1996.

Wierzba, A., et al., "Production and properties of a bifunctional fusion protein that mediates attachment of vero cells to cellulosic matrices," *Biotechnology and Bioengineering*, 47:147-154, 1995.

\* cited by examiner

FUSION PROTEIN MICROARRAYS AND METHODS OF USE

RELATED APPLICATIONS

This application claims the benefit of priority under 35 U.S.C. § 119(e) to U.S. Provisional Application 60/254,516, filed Dec. 8, 2000, the entire contents of which is incorporated herein by reference.

FIELD OF THE INVENTION

The invention relates generally to protein microarrays and specifically to fusion proteins having a polyanionic domain used to produce protein microarrays.

BACKGROUND

Systematic efforts to identify and understand protein function and structure have been facilitated by miniaturized assays that use extremely low sample volumes, yet allow for rapid and simultaneous analysis of thousands of proteins. Such "high through-put" miniaturized technology was first developed for studying nucleotide sequences. While much of the methodology used to design and prepare oligonucleotide arrays can be used with proteins, certain protein-specific challenges remain.

Screenings for proteins have typically been carried out by screening large numbers of random cDNA libraries. Traditional library screening techniques required the preparation of expressed proteins in phage vectors followed by immobilization of the protein on a membrane by a plaque lift procedure. This method is effective but is limited for several reasons. Clones do not always encode proteins in the correct reading frame and most proteins are not full length. Furthermore, in the bacterial expression system, abundant transcripts can often be overexpressed, while some proteins with low transcript number are not expressed at all. In addition, the bacterial system does not always permit the protein to be folded correctly.

High-throughput molecular biology techniques for identifying clone genes allow for DNA microarrays to study a variety of cloned genes. The genes can be attached to the surface of a support by physical or chemical means. The attached oligonucleotides may be in a random or pre-determined attachment orientation. For example, an oligonucleotide can be attached to support surface at the 5'- or 3'-end.

Certain aspects of microarray technology designed for oligonucleotides can be used to study proteins. The different physical and chemical properties of proteins as compared to oligonucleotides, however, requires new approaches. One key factor in producing protein microarrays is the mechanism for immobilizing and attaching proteins to a support. The method used should maintain protein function when function is being assayed, or protein structure when structure is assayed.

There is thus a need for means of attaching subject proteins to supports for use in a microarray. The present invention meets that need and more.

SUMMARY OF THE INVENTION

In one embodiment, the invention provides a fusion protein including a protein and a polyanionic domain attached to the protein at a terminal region.

Another embodiment of the invention provides a method for non-covalently attaching a protein to a solid support. The method includes (a) fusing to a terminus of the protein, a polyionic protein to form a fused protein; (b) applying a polycationic coating to the solid support; and (c) dispensing the fused protein in solution to the solid support.

Still another embodiment of the invention provides a protein microarray produced by (a) fusing to a terminus of the subject protein, a polyionic protein to form a fused protein; (b) applying a polycationic coating to the solid support; and (c) dispensing the fused protein in solution to the solid support.

Yet another embodiment of the invention provides a microarray. The microarray includes a solid support having a polycationic coating; and one or more fusion proteins non-covalently attached to the solid support in orderly discrete spots.

DETAILED DESCRIPTION OF THE INVENTION

Figure 1A:
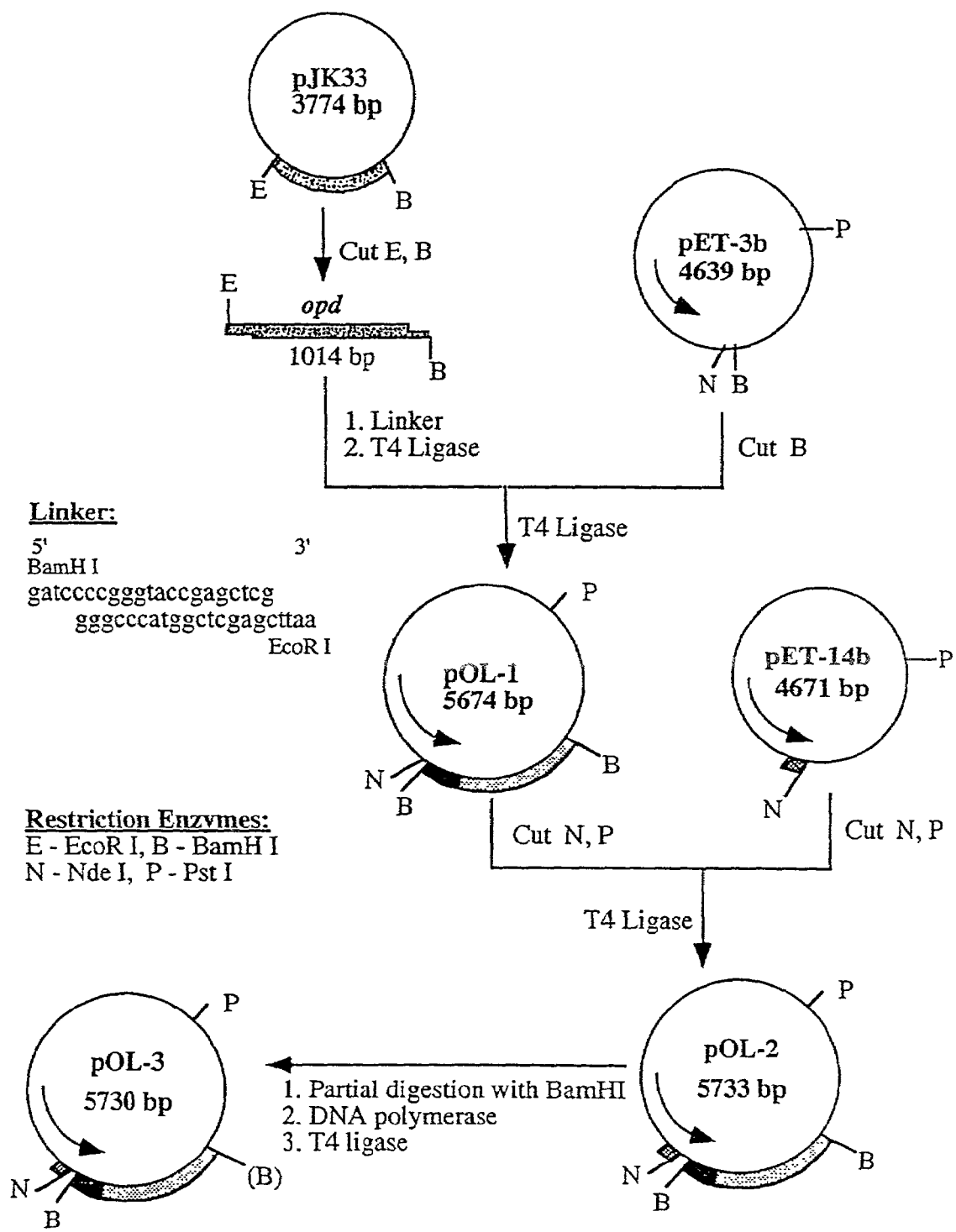
FIGS. 1A and 1B show a schematic diagram of a DNA construct for the expression of fusion proteins.

The present invention provides a protein fusion approach to protein microarrays. Fusion proteins having a protein of interest fused in the terminal region to a protein are created. The protein has a polyanionic domain that binds to a cationic coating on a solid support. Fusion proteins are dispensed to a polycationic-coated solid support to provide an array of discrete, identifiable droplets.

Fusion proteins contain two or more separately identifiable proteins or protein domains attached to one another. As used herein, "fusion protein" refers to a protein that contains a subject protein and a domain protein attached to one another. Proteins are typically composed of two or more domains, often separately folded, that are joined together. Fusion proteins can be synthesized by methods known to those of skill in the art including solid phase protein synthesis, and by molecular techniques that permit the manipulation of DNA in vitro, including polymerase chain reaction (PCR) and oligonucleotide-directed mutagenesis (see Examples section).

Protein domains generally confer specific functional or structural properties on the protein. Protein domains can function by directing specific interactions with ligands, receptors, or other molecules. Protein domains can also be engineered to confer specific physical or chemical properties on the fusion protein. A protein domain can include amino acid residues that are hydrophobic or hydrophilic, ionic or non-ionic, and the like. A domain having ionic amino acids provides a charged region to the protein. A charged domain can be anionic or cationic. As used herein, "a polyanionic domain" refers to a protein domain having more anionic amino acids than cationic amino acids. A polyanionic domain can contain about 1 to about 40 anionic amino acid residues. Anionic amino acids include amino acids having a negatively charged side chain such as glutamic acid, aspartic acid, and the like. A polyanionic domain can contain one type of anionic amino acid such as one or more aspartic acid residues, or one or more glutamic acid residues, or can contain a combination of anionic residues, such as aspartic acid and glutamic acid. Polyanionic domains can contain cationic amino acids as well as non-ionic amino acids as long as the total charge of the domain is negative. As used herein, "a polycationic domain" refers to a protein domain having more cationic amino acids than anionic amino acids.

Polyanionic domains contain anionic amino acid residues, cationic amino acid residues, and non-ionic amino acid residues. Exemplary polyanionic domains have the formula -[-(Ala-Gly)$_x$-Pro-Glu-Gly-]-$_n$ (SEQ ID NO:1). The variable x is 0, 1, 2, 3, 4, 5, 6, 7, or 8, and the variable n is an integer from about 1 to 40. For example, a polyanionic domain includes a domain having the formula -[-(Ala-Gly)$_x$-Pro-Glu-Gly-]-$_n$, where x is 3 and n is 16, and where x is 3 and n is 36. Additional exemplary polyanionic domains have the formula -[-(Ala-Gly)$_x$-Glu-Gly-]-$_n$ (SEQ ID NO:2). In this formula, the variable x is 0, 1, 2, 3, 4, 5, 6, 7, or 8, and the variable n is an integer from about 1 to 40. For example, polyanionic domain include a domain having the formula -[-(Ala-Gly)$_x$-Glu-Gly-]-$_n$, where x is 4 and n is 16, 18 or 28, where x is 5 and n is 14, and where x is 6 and n is 14.

A polyanionic domain is attached to the subject protein at a terminal region of the subject protein. As used herein, "terminal region" refers to a continuous amino acid sequence of about 30 amino acids, one of which is a terminal amino acid. The terminal amino acid can be the amino acid at the amino-terminal, and the terminal region is the amino-terminal region, and the terminal amino acid can be the carboxyl terminal region, and the terminal region is the carboxyl-terminal region. In certain embodiments, the polyanionic domain is attached to the subject protein at the terminal amino acid.

Subject proteins can be any naturally occurring or artificial protein. Proteins perform versatile biological functions with high activity and specificity under mild reaction conditions and they are biodegradable and environmental friendly. Proteins have been used for centuries in the food industry, and more recently, in the pharmaceutical and chemical industries as well. Modern genetic engineering procedures have made it possible to produce natural and artificial proteins in large quantities, and to modify their primary structures, with concomitant control of physico-chemical and biological characteristics. The invention provides a fusion protein containing the subject protein, and a protein microarray that allows subject proteins to be assayed in numerous ways. Therefore, any protein contemplated for use in a microarray can be a subject protein. Protein arrays can be used for detection and assessment of a range of interactions including protein-protein, protein-RNA and protein-DNA.

Protein interactions with other proteins play pivotal roles in gene expression, developmental mechanisms, metabolic pathways, immune responses, intracellular protein trafficking, amongst many others. Protein arrays containing interacting proteins of any type are contemplated in the present invention. Such proteins include enzymes, antibodies, transcription factors, signal transduction factors, growth factors, toxins, hormones, structural proteins, transport proteins, pesticides, and the like.

One protein-protein application of a protein array is an array designed for simultaneous immunoassay testing for the presence of multiple antigens in a mixture. This type of assay can utilize small amounts of antibodies, each antibody being immobilized as a discrete spot on a solid support. The antibodies bind to or "capture" antigen in the mixture. The antibody can be labeled with a fluorescent maker and the presence of a captured antigen can be assessed with a labeled sensing antibody that binds to the captured antigen, or by determining unoccupied binding sites.

Fusion proteins employed in invention micro arrays are substantially purified. As used herein, the term "substantially purified" or "substantially pure" or "isolated" means that the molecule being referred to, for example, a protein or a fusion protein, is in a form that is relatively free of proteins, nucleic acids, lipids, carbohydrates or other materials with which it is naturally associated. Generally, a substantially pure protein constitutes at least twenty percent of a sample, generally constitutes at least about fifty percent of a sample, usually constitutes at least about eighty percent of a sample, and particularly constitutes about ninety percent or ninety-five percent or more of a sample. A determination that a protein of the invention is substantially pure can be made using well known methods, for example, by performing electrophoresis and identifying the particular molecule as a relatively discrete band. A substantially pure protein can be obtained, for example, by a method of chemical synthesis, or using methods of protein purification, including purification by chromatographic or electrophoretic methods.

In another embodiment of the present invention, there is provided a method for non-covalently attaching a subject protein to a solid support. The method includes (a) fusing to a terminus of the subject protein, an artificial polyanionic protein thereby forming a fused protein; (b) applying a polycationic coating to the solid support; and (c) dispensing the fused protein in solution to the solid support.

An invention method step includes fusing a subject protein to an artificial polyanionic protein. The proteins are connected by adding the artificial polyanionic protein to the subject protein at a terminus of the subject protein. The carboxyl terminus or the amino terminus of the subject protein can be used for attachment depending on the region of interest in the protein. The region adjacent to the terminus that is the attachment site, about ten to about 30 amino acids, may be less exposed to the surface than the other terminus. Thus, the attachment terminus can be the terminus that is further from the area of interest, for example, a binding site, a catalytic site, an epitope site, an identifying or non-identifying motif site.

Protein fusion can be accomplished using recombinant DNA techniques that permit production of designer proteins. With advances in recombinant DNA technology, fusion proteins have been made readily through manipulation of the genes of different proteins, by "cutting and pasting" of restriction fragments, and subsequently producing target proteins in living organisms. Strategies for producing and expressing fusion proteins are allowed by techniques for manipulation of DNA in vitro, such as polymerase chain reaction (PCR) and oligonucleotide-directed mutagenesis, as well as automated DNA sequencing techniques. The bacterium *Escherichia coli* is typically used as a host organism, although many others can be employed with success. The resulting fusion proteins, in many cases, exhibit the individual biological activities of each protein domain. Fusion proteins thus provide opportunities for rearrangement of natural proteins to combine properties from different proteins, and ultimately, to execute multiple functions in a single polypeptide.

Fusion proteins have the structures composed of a subject domain (also referred to herein as a "natural domain") and a second domain. Preferably, a fusion protein of this invention has a subject domain and an artificial domain. The subject domain is a naturally occurring protein (e.g., enzyme or antibody) and it is fused to an artificial domain that exhibits desired material properties. Through the de novo design of artificial domains to confer useful and versatile materials properties, the fusion proteins lead to novel structures and functions and allow material scientists to harvest biological activities in the forms of particles, films and membranes.

Exemplary fusion proteins include: (1) self-assembling protein arrays. When repetitive polypeptides self-assemble into well-defined secondary structures (e.g., β-sheets or α-helices), the natural domain aggregates in a regular pattern on the surface of the artificial peptide matrix; (2) bioreactive surfaces. When the artificial polypeptide is designed to carry multiple functional groups that promote interaction (e.g., physical adsorption and chemical bonding) with surfaces; the natural domain partner retains biological function (e.g., enzyme for biocatalytic activities, or cell recognition domains to promote cell adhesion and proliferation, etc.); (3) enzyme networks. With the artificial domains forming crosslinked structures and the other enzymatic domain embedded in the network, the fusion protein could produce an "enzyme gel." The crosslinking density and the mechanical strength of the gel could be varied with polypeptide functional groups and chain sequence. For example, by designing the polypeptide sequence, polymeric gels will undergo conformational changes with pH or temperature. Enzymatic reactions within the gel could be controlled by diffusion of the substrate from solution into the gel; (4) selective membranes. When the artificial domain self-assembles into membrane structures, the natural partner acts as transport proteins that selectively transport molecules (ions, small proteins, and the like) across the artificial membranes.

The solid support is prepared by applying a polycationic coating to the solid support. As used herein. "polycationic coating" refers to a layer of a material that has an overall positive charge. The material is applied to the solid support such that a layer is deposited over the surface of the solid support in a relatively uniform manner. Polycationic coating materials include polyamino acids. Polyamino acids are mixtures of polymer chains differing in the degree of polymerization. The polyamino acid can be a homo-polyamino acid such as poly-L-lysine, or a random copolymer or a specific copolymers.

The polyanionic coating can be applied to the solid support by a variety of methods. For example, the solid support can be dipped one or more times into the coating material. The material can be applied as a film or sheet over the surface of the solid support. The coating material can be rolled, brushed or sprayed onto the solid support.

The solid support can be any material to which a polycationic coating can be applied. Exemplary solid support materials include glass, for example, glass slides, dishes, and plates, metal, plastic, solid polymer material such as polypropylene, polystyrene, and the like, and the like.

The fused protein in solution is dispensed to the solid support. The protein, in any aqueous or non-aqueous solution, is dispensed to the solid support having a polycationic coating. Dispensing can be done by any method that results in the deposition of protein solution in a discrete, identifiable droplet. Exemplary methods include printing, blotting, electrode-directed, and the like methods.

One method of dispensing and depositing proteins to the support surface uses printing techniques to deposit or spot nanoliter (nL) to picoliter (pL) volumes of protein into regular patterns with micrometer (μm) to millimeter (mm) distances between the spots. Ink-jet printers can be adapted to print at defined locations by filling the printer head with the protein to be spotted. The three main types of ink-jet dispensers (e.g., piezoelectric, solenoid and thermal) differ in how the liquid is ejected through a small hole as a droplet (Lemmo et al., (1998) *Current Opin. Biotech.*, 9:615-617).

In the thermal type, the fluid is heated, causing a vapor bubble to form, expand and be ejected. The solenoid type uses gas or hydraulic pressure to compress the fluid against a valve so that when the valve is opened, an acoustic or pressure wave is generated allowing fluid dispensing. Finally, the piezoelectric type uses a piezoelectric crystal coupled to a fluid reservoir. Changing the crystal dimension causes the reservoir to compress and eject the liquid from the reservoir. A piezoelectric dispenser can deliver small drops of fluid with volumes ranging from 30 to 500 pL within a 40 to 100 μm spot diameter, at a delivery rate of one to more than 1000 drops per second. Recently bubble jet technology, commonly used for printers, has been employed for fabrication of oligonucleotide microarrays on glass surfaces. The problems of exposing and consequently damaging the oligonucleotides at the high operating temperature (200° C.) and shearing stress were addressed using a specially formulated diluent (Okamoto et al. (2000) *Nature Biotechnology* 18: 384-385).

Flat-tipped stainless steel pins (0.4-0.5 mm diameter, 50 nL transfer) provide another means of printing probe onto substrates such as nylon membranes (e.g. 0.75 mm center to center with 0.35 mm empty space between spots). The amount of probe deposited at individual spots is determined by the number of applications by the pin at each location (Drmanac and Drmanac (1999) *Methods in Enzymology* 303: 165-178).

Proteins can be attached to the surface of the solid support by non-covalent or covalent bonds. Non-covalent attachment of fusion proteins can be achieved by the polyanionic domain. The polyanionic domain contains at least one, and, typically, more than one negatively charged side chains. Such side chains are available to ionically interact with the positively charged cationic coating of the solid support. Hydrophobic interactions can also play a role in attachment of fusion proteins to the surface of the solid support.

Covalent attachment methods involve an initial activation of the substrate surface to provide appropriate reactive functional groups, followed by reaction with chemical groups on the probe to be immobilized at the particular spot. Hydroxyl groups on a glass surface can be activated using different types of silanizing reagents; for example, pre-synthesized 3'-amino-modified oligonucleotides can be covalently attached to the surface of a glass microscope slide epoxidated using 3'-glycidoxy propyltrimethyloxysilane. Alternatively, a polypropylene surface can be aminated by radiofrequency plasma discharge in the presence of ammonia gas and the amino groups then provide a site for subsequent covalent attachment chemistry (Matson et al. (1994) *Analytical Biochemistry* 217(2):306-310).

Covalent attachment can also be achieved by first coating the surface with a substance rich in reactive amine groups. and then using a homo-bifunctional crosslinker such as glutaraldehyde or 1,4-phenylene diisothiocyanate to link 5'-amino-modified oligonucleotides to amino groups on the activated surface. Other route to covalent attachment involves first coating the surface with polyacrylamide. This can be activated by converting some of the amide linkages to hydrazides by reaction with hydrazine. Next, the 3'-terminal 3-methyluridine sugar of an oligonucleotide is oxidized using periodate to form a reactive aldehyde. The aldehyde then reacts with the hydrazine groups on the immobilized polyacrylamide gel (Khrapko et al. (1991) *DNA Sequence* 1(6): 375-388). Other attachment methods developed specifically for cDNAs involve denaturation of the cDNA in alkaline solution, followed by deposition onto a poly-1-lysine-coated glass slide and ultraviolet (UV) irradiation and/or by overnight drying to physically-chemically bond the fragments to the coated slide (Schena et al. (1995) *Science* 270(5235):467-470). DNA methods may be adaptable to protein microarrays.

Also provided by the invention is a protein microarray. As used herein, "microarray" refers to a collection of proteins arranged on a substrate, such as paper, nylon or other type of membrane, filter, gel, polymer, chip, glass slide, or any other suitable support.

Multispot microarrays provide a simple means of performing tens to hundreds of thousands of analytical reactions using a relatively small test device. Various testing options are possible. The test samples can be arrayed and reacted with one or more analytical reagents (dot blot assay design), or a collection of probes can be arrayed and exposed to a test sample (reverse dot blot assay design). Two-color labeling schemes permit simultaneous assessment of the reaction of targets derived from two different sources (e.g. test and control or reference). A further high-sensitivity assay principle utilizes a ratio-metric immunoassay design in which an immobilized labeled antibody, present in increasingly smaller amounts, captures analyte, and the occupancy of the capture antibody is determined using a labeled sensing antibody (see Ekins and Chu (1991) *Clinical Chemistry* 37(11): 1955-1967 and above).

The multispot array format has also been adapted for parallel, high throughput analysis of proteins so that thousands of functionally, previously noncategorized proteins can be eventually arranged into a specific biological pathway. Arrays can also be used to identify protein-protein interactions, and specific interactions of proteins with DNA, RNA, ligands and small molecules (e.g. for drug discovery) (Ge H (2000) *Nucleic Acids Research* 28(2): e3).

Arrays can be created that contain specific classes of subject proteins, random collections of subject proteins, or the same subject protein. For example, an array can contain multiple iterations of a subject protein, with each iteration being fused to a different polyanionic domain. The length, three-dimensional size, and charge of the polyanionic domain can result in presentation of the subject protein in a variety of ways. The folding of the fusion protein into a three-dimensional structure, and the amino acid sequences exposed on the protein surface can, for example, vary depending on the polyanionic domain attached.

Without further elaboration, it is believed that one skilled in the art can, using the preceding description, utilize the present invention to its fullest extent. The following examples are to be considered illustrative and thus are not limiting of the remainder of the disclosure in any way whatsoever.

EXAMPLE 1

Production of Fusion Proteins Having Enzymes as the Subject Domain

Enzymes can be immobilized by a number of techniques (see Messing, *Immobilized Enzymes for Industrial Reactors* (Academic Press, New York, 1975), including covalent bonding, crosslinking, physical adsorption and entrapment in gels or membranes. Immobilized enzymes have been used as heterogeneous biocatalysts in industrial processes including racemic separation, production of high-fructose corn syrup, and hydrolysis of lactose in milk. More recently, immobilized enzymes have been applied in biosensors that are finding increasing use in medicine, food quality control and environment monitoring. For each specific enzyme, developing an immobilization technique without loss of enzymatic activity can be time consuming and difficult for sensitive enzymes.

Genetically engineered affinity domains have been fused to proteins to facilitate enzyme immobilization (Ljungquist et al., *Eur. J. Biochem.*, 186:563-569 (1989), Ong et al., *Bio/technology*, 7:604-697 (1989) and Sassenfeld, *Trends Biotechnol.* 8:88-92 (1990)). Such fusion proteins could be immobilized by taking advantage of the specific binding of the affinity peptide to an affinity adsorbent, while the partner domain exhibits biological activity on the surface (Hentz and Daunert, *Anal. Chem.* 68:3939-3944 (1996)). Such fusions allow immobilization of enzyme without denaturation and with retention of high catalytic activity.

A fusion protein has been constructed for enzyme immobilization by fusing a gene for a β-glucosidase (Abg) and part of the gene for an exoglucanase ($CBD_{Cex}$) (see Ong et al., supra). The fusion protein (Abg-$CBD_{Cex}$) exhibited the cellulose-binding properties of Cex and β-glucosidase activity of Abg and retained 42% of the β-glucosidase activity when bound to cellulose. The sequence Arg-Gly-Asp (RGD) in extracellular matrix proteins such as fibronectin, collagen, and laminin mediates cell attachment by interacting with proteins of the integrin family of cell surface receptors. The same research group recently reported fusion of CBD/RGD as a linking molecule between a cell and a cellulose surface (Wierzba et al., *Biotech & Bioeng.*, 47:147-154 (1995)). Protein A was fused with β-lactamase and adsorbed on IgG-coated Sepharose matrices with higher specific activities and lower $K_m$ values relative to covalently immobilized β-lactamase. Adsorption of the fusion protein on the support resulted in increased stability to thermal deactivation. An affinity chromatography system using a fusion protein which contained calmodulin (CaM) and protein A (ProtA), was immobilized on a solid support containing phenothiazine through CaM, while Protein A at the N-terminus serves as the affinity site for a heat shock protein. The target protein is released upon addition of ATP and the affinity column can be easily regenerated by elution of the immobilized fusion with addition of EGTA and reloading of fresh ProtA-CaM.

The above described fusion proteins were immobilized by interactions of the affinity domain with surfaces through the specific recognition processes drawn from nature, e.g., antibody-antigen, enzyme-substrate or receptor-ligand interactions. Oligopeptides containing multiple amino acid residues have also been used for protein immobilization through functional groups on the side chain of the residues. Hochuli and coworkers used Amino-terminal hexahistidine fusion proteins to immobilize β-galactosidase to the Ni2+-nitrilotriacetic acid adsorbent (Piesecki et al. Biotech & Bioeng. 42:178-184 (1993)). The fusion protein retained 64% of its β-galactosidase activity when bound to the adsorbent. Allyl-β-D-galactopyranoside was synthesized from lactose and allyl alcohol on a gram scale by the immobilized β-galactosidase. Another example is provided by a fusion protein that contains a polycationic hexa-arginine and an Amino-terminal yeast α-glucosidase (Stempfer et al., Nature Biotech, 14:481-484 (1996)). This fusion protein can be directly adsorbed from crude cell extracts on polyanionic matrices. Upon immobilization, the stability of the fusion protein is not affected by pH, urea, or thermal denaturation. The immobilized enzyme was used in column reactors for production of carbohydrates with good operational stability.

The present data supports biological synthesis of polymeric materials to achieve well-defined molecular architecture including precisely controlled sequence, predetermined chain length, monodispersity, and suitable stereochemistry. By applying the principles of materials science and structural biology, protein-based polymers have been synthesized with lamellar crystal structures, novel liquid crystal behavior and defined functional groups on surfaces. Given these successes in the design and synthesis of polymeric materials with defined structural properties and surface functions, fusion proteins as novel biocatalytic materials to improve practical applications of natural proteins can be produced.

Fusion proteins can be designed where the artificial domain serves to bind to surfaces while the subject domain performs a biologic function. For example, the subject protein can be an enzyme that performs a catalytic function. Versatile protein-surface interaction could be realized by variation of chemical properties of the artificial domains. In order to achieve the desired properties, the artificial domain must fulfill the following requirements: (i) useful chemical properties; e.g., functional groups at precise positions to promote adhesion of the proteins to surfaces and mechanical and physical stability. The natural protein domain, on the other hand, should have the following character: (i) useful biocatalytic functions; (ii) tolerance towards modification (fusion of artificial domain); (iii) ease of assay for activity.

A family of artificial ionic domains can be used to gain control over chain length, chemical and structural properties:

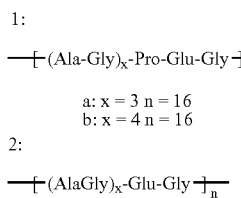

Such polypeptides can be produced in *E. coli* in good yield and have been shown to adopt random coil or β-sheet structures (Krejchi et al. Science, 265:1427-1432 (1994) and McGrath et al., J. Am. Chem. Soc. 114:727-733 (1992). The periodic acidic side chains from the glutamic acid residues provide affinity to basic surfaces. The natural domain is a bacterial phosphotriesterase which catalyzes rapid hydrolysis of organophosphorus pesticides and nerve agents. The phosphotriesterase used here contains the modified amino acid sequence reported by Mulbry and coworkers, which is characterized by deletion of the 33 Amino-terminal amino acids of the native enzyme (from native sequence of *pseudomonas diminuta*) and replacement by the first 5 lac Z residues (Met-Ile-Thr-Asn-Ser-) (SEQ ID NO:3) followed by the enzyme residues (-Gly-Asp-Arg- (SEQ ID NO:9)), in order to achieve significant improvements in the enzymatic activity in *E. coli* (Mulbry and Karns, J. Bacteriol. 171:6740-6746 (1989)). The activity of the enzyme can be easily determined using the pesticide paraoxon as substrate. Paraoxon can be enzymatically degraded to release a brightly colored phenolic product with a maximal absorption at 400 nm (Omburo et al., J. Biol. Chem. 267:13278-13283). The enzyme shows good stability and unusually high enzymatic activity, exhibiting a rate near the diffusion limit with substrate paraoxon (Caldwell et al., Biochemistry, 30:7438-7444 (1991)). The fusion proteins containing the repetitive polypeptides and phosphotriesterase adsorb to basic surfaces through the acidic artificial domain while the partner enzyme catalyzes hydrolysis of organophosphates.

EXAMPLE 2

Materials and Methods

The vectors pET-3b and pET-14b were purchased from Novagen. Restriction enzymes BamH I, EcoR I, Pst I and Nde I as well as T4 ligase and DNA polymerase were obtained from New England Biolabs. Ampicillin, Chloramphenicol, paraoxon (diethyl-p-nitrophenyl phosphate), (3-cyclohexylamino)-1-propanesulfonic acid (CAPS), 2-(N-cyclohexylamino)ethanesulfonic acid (CHES), (N-2-hydroxylethylpiperazine)-N-2-ethanesulfonic acid (HEPES), (2-N-morpholino)-ethanesulfonic acid (MES) were purchased from Sigma Chemical Company. All reagents except paraoxon were used as received. Paraoxon was purified by dissolution in dichloromethane followed by extraction with 10 mM CHES buffer, pH 9.0 according to a reported procedure (Omburo et al., supra). The purified paraoxon was dissolved in water in a final concentration of 0.5 mM and stored at 4° C. All the DNA manipulations were performed according to standard procedures (see Sambrook et al., Molecular Cloning: A Laboratory Manual, 2nd edition, Cold Spring Harbor Laboratory Press, Cold Spring Harbor, 1989). Isopropyl-β-thiogalactoside (IPTG) was obtained from Calbiochem. Ni-NTA resin was purchased from Qiagen, Inc. Econo-Pac 10DG was obtained from Bio-Rad, Inc. DEAE Sephadex A-50 and A-25, and QAE Sephadex A-50 were purchased from Pharmacia Inc. Centriprep 10 ultrafiltration units were from Amicon Division, W. R. Grace & Co. Protein-Pak DEAE was obtained from Waters Inc.

Figure 1B:
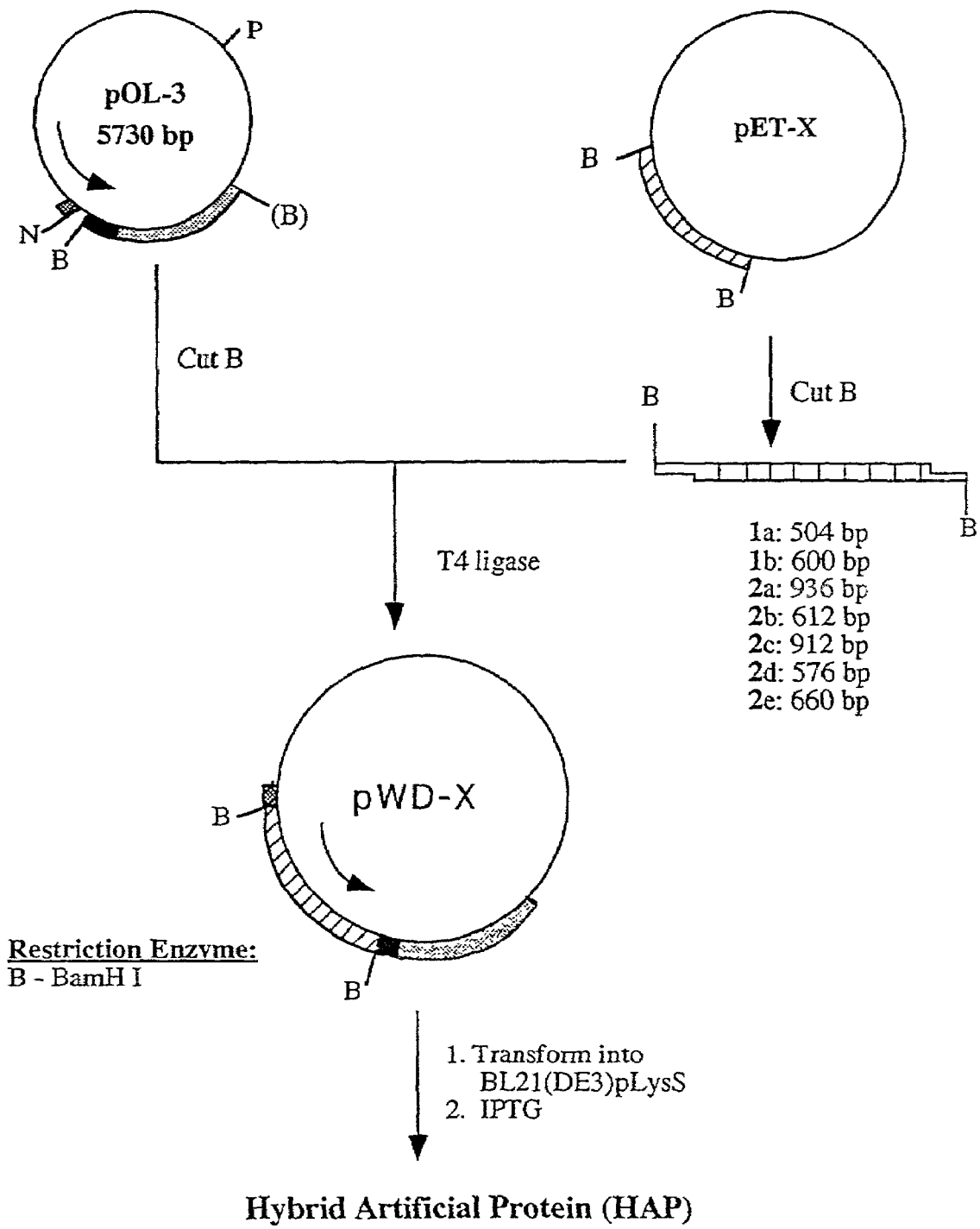

Recombinant DNA Construction. Construction of the recombinant DNA encoding the fusion proteins is schematically shown in FIG. 1. Plasmid pJK33 (obtained from Professor Frank Raushel of Texas A&M University) was digested with restriction enzymes BamH I and EcoR I. The resulting 1014 base pair subcloned opd gene encoding the phosphotriesterase was isolated from an agarose gel. The opd gene was ligated with a 21 base pair linker prepared by digestion of pUC18 with BamH I (SEQ ID NO:4) and EcoR I (SEQ ID NO:5). pET-3b was digested with BamH I to yield a linear fragment, which was purified on a 1% agarose gel. The linearized pET-3b fragment was combined with the linker modified opd gene (1:5 molar ratio) and incubated with T4 ligase at 15° C. overnight. The resulting recombinant DNA plasmid (designed pOL-1) was transformed into bacterial strain HB101. Colonies were screened for insertion and insert orientation by digestion with BamH I (supposed to yield 1035 base pair and 4639 base pair fragments) and EcoR I (supposed to yield 1524 and 4150 base pair fragments). pOL-1 was digested with Nde I and Pst I and the 2334 base pair DNA fragment was isolated by electrophoresis on a 1% agarose gel. pET-14b was digested with Nde I and Pst I and the 3399 base pair DNA fragment was purified as described above. The two gene fragments were incubated with T4 ligase, and the ligation product was used for transformation of *E. coli* strain BL21(DE3)pLysS. Transformants were selected and the DNA was verified by Ava I digestion (supposed to yield fragments of 486, 1254 and 3993 base pair). The resulting plasmid (pOL-2) was partially digested with BamH I and the 5733 base pair fragment was incubated with DNA polymerase followed with ligation with T4 ligase to destroy the BamH I site on the 3' end. The plasmid was designated pOL-3. A family of fragments encoding the artificial domains was obtained from BamH I digestion of corresponding recombinant plasmids 21, 22, 28 and the appropriated fragment was inserted in the BamH I site of pOL-3. The resulting plasmids (pWD-X) contain a series of artificial coding sequences ligated in frame to the 5' end of the DNA encoding the modified phosphotriesterase of Mulbry and coworkers. Plasmids pWD-X were used to transform *E. coli* strain BL21(DE3) pLysS.

Expression of Fusion Proteins. Cells containing the recombinant plasmid were grown in 2 liters of rich tryptone-phosphate medium (Moore et al., Protein Expression Purif., 4:160-163 (1993)) supplemented with 200 mg/ml Ampicillin, 25 mg/ml Chloramphenicol and 0.5 mM $CoCl_2$ at 37° C.

When OD600 reached 0.8-1.0, protein expression was initiated by addition of IPTG to the medium to a final concentration of 0.4 mM. The growth temperature was then lowered to 30° C. After 6 hours, OD600 reached around 1.2-1.5, corresponding to 4-5 g of cells (wet weight) per liter of culture. Cells were harvested by centrifugation at 5,000×g for 10 minutes at 4° C. Cell pellets were resuspended in 40 ml of ice-cold sonication buffer (50 mM sodium phosphate buffer pH 8.0, 300 mM NaCl, 0.1 mM $CoCl_2$ and 0.1% Triton X-100) and stored at −80° C. until purification. Protein expression was monitored by SDS-PAGE at intervals of Protein Purification After addition of DNase and RNase to final concentrations of 10 μg/ml respectively, the frozen bacterial cells were thawed at 37° C. for 90 minutes. When cells didn't appear to be lysed completely—i.e., if the solution was not viscous—cell mixtures were sonicated on ice in 5 seconds pulse for 10 minutes. The following steps were performed at 4° C. A clarified cell lysate was obtained after centrifugation at 12,000×g for 30 minutes, and added to 8 ml Ni-NTA agarose resin pre-equilibrated with sonication buffer. The mixture was stirred gently for 2 hours. The resin was collected by centrifugation at 5,000×g for 5 minutes and packed into a polypropylene column (1.6 cm i.d.). The column was washed with sonication buffer until no significant decrease in OD280 was detected in the eluent (approximately 120-150 ml). The resin was then washed with 80-100 ml of wash buffer (50 mM sodium phosphate buffer, 300 mM NaCl, 0.1 mM $CoC_2$, 10% glycerol, pH 6.0). Further washes were conducted with Tris buffer, pH 7.9 containing low concentrations of imidazole: 50 ml MCAC-0 buffer (20 mM Tris Cl, pH 7.9, 500 mM NaCl, 0.1 mM $CoCl_2$), 50 ml MCAC-5 buffer (MCAC-0 buffer, 5 mM imidazole), 30 ml MCAC-20 buffer (MCAC-0 buffer, 20 mM imidazole).

The target protein was eluted with 4×3 ml MCAC-200 buffer with most target protein eluting in third and fourth fractions. The eluent was immediately subjected to buffer exchange into HEPES buffer (50 mM HEPES, pH 8.5, 10% glycerol and 0.1 mM $CoCl_2$) using a Bio-Rad pre-packed Econo-Pac 1ODG column. The protein solutions were combined and loaded on a Sephadex DEAE A-50 column (5.0× 1.6 cm). The column was washed with 40 ml HEPES buffer, 60 ml HEPES-50 (HEPES buffer containing 50 mM NaCl), and eluted with 40 ml volumes of HEPES-100 buffer and HEPES-300 buffers. The eluted fractions were concentrated to ca. 1 mg/ml by ultrafiltration using a Centriprep 10 unit. Proteins were analyzed by electrophoresis on 12% SDS-polyacrylamide gel. Quantitative measurements of protein concentration were made achieved by the Bradford method with BSA as standard.

Enzyme Activity Measurements. For the soluble proteins, enzymatic activity was measured using paraoxon as the substrate in 150 mM CHES buffer at pH 9.0. The reaction was monitored through the absorbance of the product p-nitrophenolate anion (λmax 400 nM, $\epsilon=17,000$ $cm^{-1}$) on a Hitachi Model 2600 spectrophotometer. One unit of activity is defined as the amount of enzyme that hydrolyzes 1 μmol of paraoxon per minute. For the immobilized enzymes, the substrate of interest was treated with the fusion protein and then suspended in 150 mM CHES buffer at pH 9.0. Enzyme activity was monitored through the absorbance at 400 nm upon addition of substrate paraoxon.

The initial reaction velocity was measured for paraoxon with concentrations ranging from 0.025 to 1.5 mM. The kinetic constants were determined from the Michaelis-Menten equation as follows: $V=VmS/(Km+S)$; where V is the initial velocity, Vm the maximal velocity, S the substrate concentration and Km the Michaelis constant. The kinetic constants were determined by at least three independent measurements, with twelve paraoxon concentrations in each measurement.

The rate of enzymatic hydrolysis of paraoxon (1 mM) was determined for both the soluble and immobilized forms of the phosphotriesterase at pH values from 4 to 11. The pH value was controlled with the following buffers (100 mM sodium acetate buffer, pH 4.0, pH 5.0; 100 mM MES, pH 6.0; 100 mM MOPS, pH 7.0; 100 mM HEPES, pH 8.0; 100 mM CHES, pH 9.0; and 100 mM CAPS, pH 10.0 and pH 11.0)

Procedure for Immobilization on Resin. Sephadex DEAE A-25, Sephadex DEAE A-50, QAE A-50 and Protein-Pak DEAE were tested as substrates for immobilization of the fusion protein. The resins were pre-equilibrated with HEPES buffer and dried at room temperature. The fusion protein solution was added to the resin and incubated at 4° C. overnight. The resin was washed extensively with HEPES buffer until no activity was detected in the wash, and then resuspended in HEPES buffer. The extent of immobilization was determined from the difference between the amount of enzyme added to the suspension and the amount present in the wash solutions. Protein adsorption was also determined from the difference between the activity incubated with the beads and that in the wash.

Activity upon Repeated Use. An aliquot of the immobilized fusion protein on DEAE Sephadex A-50 was resuspended in 150 mM CHES buffer, pH 9.0, in the filter of a Spin-X centrifuge unit (0.2 μm). Paraoxon was added to start the hydrolysis reaction, and the supernatant was isolated after 5 seconds by centrifugation. The absorbance of the supernatant was measured at 400 nm. The beads isolated in the upper filter were resuspended and subjected to the same procedure through 10 cycles.

EXAMPLE 3

Production of Fusion Proteins

Construction of the Bacterial Expression Systems Genes encoding a series of artificial proteins ligated to the 5' end of the opd fragment (which corresponds to residue Asn of the modified phosphotriesterase) were constructed through recombinant DNA technology. A short linker encoding nine amino acid residues was derived from the polylinker region of pUC18 and used to fuse the two fragments of genes in frame. The amino terminus of the phosphotriesterase was chosen for fusion with the artificial domain based on previous kinetic studies of the enzyme: Mulbry and Karns reported that the enzyme remained highly active with Amino-terminal deletion of 33 amino acids and replacement with the first 5 residues from lacZ, while C-terminal modification resulted in complete loss of enzymatic activity.

The crystal structure of the phosphotriesterase provides insight into the enzyme's tolerance of amino-terminal modification. The enzyme was shown to be a homodimer of α/β barrel subunits, with eight parallel β-strands forming the barrel and flanked on the outer surface by 14 α-helices. The active site of each subunit is located on the C-terminus of the β-barrel and contains two equivalents of zinc as a binuclear metal center separated by 3.3 Å. Upon formation of the dimer structure, the two active sites are located towards the interface. The two amino termini lie near the outer surface in an asymmetrical manner and are away from the active sites. The crystal structure of the enzyme provided support of the design of the fusion proteins because the addition of the artificial ionic domain at the amino-terminus does not significantly disturb the structure of the enzyme and therefore results in preservation of enzymatic activity.

A series of genes varying in length from 1641 to 2073 base pair (depending on the length of the artificial domain) were cloned in expression vector pET-14b, a T7 phage promoter-driven system originally developed by Studier and colleagues (Studier et al., Methods Enzymol., 1-60 (1990)). The recombinant plasmids were designated pWD-X, where X reflects the sequence of the artificial domain. For example, "3PEG16" represents artificial domain [(AG)3PEG]16, "3EG36" depicts artificial domain [(AG)3EG]36. Restriction analysis was conducted to verify insertion and correct orientation of the insert in the plasmid constructs. The DNA fragments resulting from BamH I digestion were 5730 base pair (all plasmids) and 504 base pair (pWD-3PEG16), 600 base pair (pWD-4PEG16), 936 base pair (pWD-3EG36), 612 base pair (pWD-4EG28), 912 base pair (pWD-4EG28), 576 base pair (pWD-5EG14) and 660 base pair (pWD-6EG14), respectively. Ava I digestion yielded fragments of 486 base pair, 4013 base pair (all plasmid) and 1735 base pair (pWD-3PEG16), 1831 base pair (pWD-4PEG16), 2167 base pair (pWD-3EG36), 1843 base pair (pWD-4EG18), 2143 base pair (pWD-4EG28), 1807 base pair (pWD-5EG14) and 1891 base pair (pWD-6EG14) in length respectively. The plasmids were used to transform $E.\ coli$ strain BL21(DE3)pLysS, the host for target protein expression.

Expression of the Fusion Proteins. (A) HAP3EG36 The first fusion protein experiments were carried out in $E.\ coli$ strain BL21(DE3) pLysS transformed with the recombinant plasmid pWD-3EG36. The fusion protein, designated HAP3EG36, contains the phosphotriesterase fused to the artificial domain $[(AlaGly)_3GluGly]_{36}$. The target protein was expressed under control of a strong bacteriophage T7 promoter recognized by the highly active T7 RNA polymerase. The rate of cell growth was monitored in comparison with control experiments using the same strain but without induction, strain BL21(DE3)pLysS pOL-3 (PTE insertion control) and strain BL21(DE3)pLysS pET-M1835 (artificial protein insertion control) conducted in tandem. The rate of cell growth prior to induction was normal in all cases, but declined in BL21(DE3)pLysS pWD-3EG36 and BL21(DE3)pLysS pET-M18 shortly after induction. The decrease of growth rate in BL21(DE3)pLysS pET-M18 (which produces the polypeptide [(AG)3EG]36) was reported previously. The growth behavior of cells that express the fusion protein very much resembles that of the strain producing the artificial domain alone.

The reduction in the growth rate appears to depend on the accumulation of a new protein (HAP3EG36) in BL21(DE3) pLysS pWD-3EG36, as the same strain without induction continued to grow at the normal rate. On the other hand, BL21(DE3)pLysS/pOL-3, which produces the recombinant phosphotriesterase (PTE), continued to grow at the normal rate after induction, indicating a lack of severe toxicity of the phosphotriesterase in the BL21(DE3)pLysS strain. Gel electrophoresis of the crude cell extracts revealed a new protein of apparent molecular weight ca. 90,000, much higher than the actual molecular weight (64,050) of the fusion protein. It is known that poly(AG)3EG migrates anomalously i.e., slowly, under similar electrophoretic conditions. This behavior has been attributed to the bias of the sequence of the artificial domain towards amino acids of relatively low molecular weight, and to the high acidity of this domain. Therefore it is not too surprising that the fusion protein, containing the artificial polypeptide, showed the same anomalous migration. HAP3EG36 was stable and showed no degradation during protein synthesis as determined by 35S methionine labeling in a pulse-chase protocol.

Whole cell lysates containing HAP3EG36 showed enzymatic activity. Paraoxon was added to protein solution in 150 mM CHES buffer, pH 9.0. The reaction mixture was subjected to successive wavelength scans as a function of reaction time. The enzymatic hydrolysis product p-nitrophenolate, as monitored by absorption at 400 nm, increased with time as the hydrolysis reaction proceeded.

Cell Growth Conditions for Improvement of Fusion Protein Production. When the fusion protein HAP3EG36 was expressed at 37° C. in 2×YT medium, SDS-PAGE analysis showed that a large portion of the fusion protein formed inactive, insoluble protein aggregate—an inclusion body. Inclusion body formation is probably due to the enzyme domain; repetitive polypeptides [(AG)3EG]36 were expressed in soluble form, while the phosphotriesterase was shown largely to form inclusion bodies when expressed in the pET vector.

One method to reduce inclusion body formation was reduction of cell growth temperature. The fusion proteins were expressed at ° C. in an attempt to reduce inclusion body formation. Although the growth was slower than that at 37° C., the HAP produced at 30° C. was more soluble and showed higher enzymatic activity in whole cell lysate. The specific activity of HAP3EG36 expressed at 30° C. was four times greater than that of samples prepared at 37° C.

The cell growth medium also affected the location of proteins expressed in $E.\ coli$. Some studies have shown that an enriched growth medium (tryptone-phosphate) could reduce inclusion body formation in the pET protein expression system. Indeed HAP3EG36 was expressed with higher specific activity when grown in tryptone-phosphate medium up to 9 hours after induction, as compared to other rich media (2×YT or 4×YT). The higher activity could also be a result of increased target protein production, as SDS-PAGE showed a significantly higher level of expression in tryptone-phosphate medium compared to 2×YT.

The phosphotriesterase is a zinc-containing metalloenzyme in its native form. It was reported that supplementing of the growth medium with 1 mM Co2+ ion increases the specific activity of the enzyme expressed in $E.\ coli$. For BL21 (DE3)pLysS cells, we found that 1 mM or 0.75 mM Co2+ was too toxic for efficient cell growth and the optical density was limited to 0.8. Different concentrations of Co2+ ion in the growth medium were tested for expression of HAP3EG36. The specific activity of the fusion protein differed significantly with cobalt concentration. The highest enzymatic activity was achieved with 0.5 mM Co2+ ion in the growth medium. However, target protein production did not seem to vary strongly with the concentration of Co2+ in the range from 0 to 0.5 mM, as judged from gel electrophoresis. This suggests that effect of the cobalt ion is to increase the fraction of active protein by yielding higher enzymatic activity of the soluble fraction and/or by reducing inclusion body formation. This argument is supported by previous reports that metal ions in metalloproteins can favorably shift the folding/unfolding equilibrium and enhance thermodynamic stability by binding with higher affinity to the folded state than to unfolded or partially folded states.

Expression of a Family of Fusion Proteins. A family of fusion proteins was produced to gain control over chemical and structural properties of the artificial domain. The proteins prepared contained the phosphotriesterase domain linked at its amino-terminus to artificial protein domains with sequences 1a-b and 2a-e respectively, where:

Sequence 1 is -[-(Ala-Gly)$_x$-Pro-Glu-Gly-]-$_n$; and
in 1a, x=3 n=16; and
in 1b, x=4 n=16.
Sequence 2 is -[-(Ala-Gly)$_x$Glu-Gly-]-$_n$; and
in 2a, x=3 n=36;
in 2b, x=4 n=18;
in 2c, x=4 n=28;
in 2d, x=5 n=14; and
in 2e, x=6 n=14.

All of the target proteins were expressed in *Escherichia coli* under control of the T7 phage promoter derived from pET-14b. The growth rates of all of the expression strains were depressed shortly after induction, correlated with the artificial protein synthesis. Protein expression was analyzed by gel electrophoresis of whole cell lysates. All the proteins, as with HAP3EG36, showed the anomalous electrophoretic migration characteristic of the artificial polypeptides. The production of fusion protein varied significantly with the sequence and chain length of the artificial domain. Most obviously, fusion proteins containing the (AG)×PEG series of artificial domains were produced more efficiently than those in the (AG)×EG series, as observed previously for the artificial polypeptides alone. The artificial repetitive polypeptides seemed also to affect proper folding of the fusion proteins. For the (AG)×EG variants, artificial domains of longer chain length were shown to produce more soluble target proteins than the shorter sequences.

From these results, it appears that cell growth and synthesis of the fusion proteins parallel the behavior similarly with the artificial domains. Many Amino-terminal fusions are used to improve heterologous protein expression. Therefore it is not too surprising that the amino-terminal artificial domain determined the biosynthesis properties of the fusion protein. Such observations will be helpful in future fusion protein designs.

Purification of the Fusion Proteins. Fusion protein HAP3PEG was chosen for further studies as the protein showed good expression in *E. coli*, almost comparable with that of the recombinant phosphotriesterase alone. Protein purification was conducted with the soluble fraction of the lysate (see Table 1 for summary of steps). Since there were six consecutive histidine residues attached to the amino-terminus of the fusion protein, the target protein was purified by immobilized metal chelate affinity chromatography. When the whole cell lysate was loaded onto a Ni-NTA resin, most *E. coli* proteins passed directly through the column but the target protein was adsorbed. After extensive washing, the target protein was eluted with a buffer solution containing 200 mM imidazole. The imidazole competed with histidine for the binding sites on Ni and subsequently displaced the target protein from the column.

TABLE 1

Purification of fusion protein HAP3PEG16

| Fraction | Total protein mg | Total activity units × 10$^4$ | Specific activity units/mg | Yield % | Purification fold |
|---|---|---|---|---|---|
| Cell lysate[a] | 612 | 5.85 | 96 | 100 | 1 |
| Ni-NTA | 23.6 | 3.95 | 1670 | 67.5 | 17.5 |
| DEAE A-50 | 5.2 | 1.84 | 3540 | 32 | 37 |

[a]Isolated from 2 liter of culture grown to a cell density of OD$_{600}$ = 1.280 and 4.5 g/L wet cell weight; the cells were grown at 30° C. after induction Imidazole was found to inactivate the fusion protein rapidly; 95% of the activity of the fusion protein were lost after incubation in 200 mM imidazole for 24 hours. A size exclusion column was used to desalt and to separate the fusion protein from imidazole in the elution buffer. The fusion protein was further purified by ion exchange on DEAE-Sephadex to homogeneity, judging from the amino acid analysis and SDS-PAGE gels. The procedure gave 2.6 mg of HAP3PEG16 per liter of cell culture (approximately 4-5 g of wet cell weight) with a 37 fold purification. HAP3PEG16 exhibited specific activity of 3540 units/mg toward hydrolysis of paraoxon, while the recombinant phosphotriesterase (PTE) showed 5630 units/mg. Therefore the fusion protein, containing additional artificial polymeric domain of 13969 Da, exhibited 63% specific activity of PTE. When normalized with molecular weight, the activity of the fusions is 85% of that of the recombinant PTE.

Phosphotriesterase from *Pseudomonas diminuta* has been purified from the a baculovirus expression system with a yield of 2.7 mg target protein from 8 grams of cells (wet weight). The specific activity of the enzyme was 3,200 units/mg. Subsequently, Omburo and coworkers purified a modified phosphotriesterase expressed in *E. coli*, with deletion of the 33 amino-terminal amino acids and replacement with the first 5 lac Z residues (Met-Ile-Thr-Asn-Ser-) followed by the Gly34 enzyme residues, with reported yield of 298 mg proteins from 160 g of bacterial cells (wet weight). The specific activity of the enzyme was 8020 units/mg using 1 mM Co2+ in the growth medium. In the present system, however, only 0.5 mM Co2+ could be used as 1 mM or 0.75 mM Co2+ was too toxic for BL21(DE3) pLysS cells to grow efficiently and the optical density was limited to 0.8. The decreased activity of the recombinant PTE prepared in this work might be a result of lower concentration of Co2+ in the growth medium. It could also be attributed to the additional 40 amino acid residues at the amino-terminus of the reported enzyme; the recombinant PTE has a molecular mass of 40,247 Da compared to 34,524 Da expressed in *E. coli* previously. The activity of the recombinant PTE is 82% of that of the reported enzyme when normalized with molecular weight of the two proteins.

The fusion proteins represents only about 3% of the whole cell proteins, calculated from the 37-fold of purification. SDS-PAGE gel, however, showed at least 25% of whole cell protein is the target protein judging from band intensity following electrophoretic analysis. Fractionation of the cell lysate and electrophoretic analysis indicated inclusion body formation of the expressed proteins. The majority of the target protein was produced in an insoluble and inactive form with only a small fraction present in the soluble lysate. The production of soluble protein was increased by using lower cell growth temperature at 30° C. and extra rich tryptone-phosphate medium. Protein purification was also conducted on the insoluble fraction of the lysate by immobilized metal chelate affinity chromatography using a denaturing protocol from Qiagen. Attempts to refold the purified inactive fusion protein from the inclusion body by dialysis with gradually decreasing concentrations of urea in 50 mM HEPES buffers was not successful.

EXAMPLE 4

Kinetic Characterization of the Fusion Proteins

Enzymatic Activity of the Fusion Proteins. Other fusion proteins also showed enzymatic activity with respect to catalytic hydrolysis of paraoxon. Of all the proteins constructed, HAP3PEG16 gave the highest specific activity (3540 units/mg). The purified HAP4EG18 and HAP4EG28 yielded specific activities of 660 and 360 units/mg respectively, suggesting that fusion proteins with smaller artificial domain was more enzymatically active.

Initial Velocity of the Enzymatic Reaction. Purified HAP3PEG16 was subjected to kinetic study using paraoxon as substrate. The hydrolysis of paraoxon was initiated upon addition of the fusion protein and monitored by measuring the increase in absorbance at 400 nm arising from the hydrolysis product p-nitrophenolate. Initially the product formation increased linearly with time, from which the initial slope can be estimated to yield an initial velocity. As the reaction proceeded, the fall in substrate concentration or/and product inhibition resulted in a velocity decrease with time. All of the kinetic studies in this work were based on measurement of the initial velocity, which is hereinafter referred to as "the reaction velocity."

Effect of Fusion Protein Concentration. The enzymatic hydrolysis of paraoxon was measured at different concentrations of HAP3PEG16 using a large excess of substrate. Under such conditions, the velocity was therefore proportional to the protein concentration. ($v=k[E]$). The reaction velocity, determined from the initial slope of the absorbance vs. time curve, indeed showed a linear correlation with the fusion protein concentration.

Effect of Substrate Concentration. The reaction velocity was measured at different concentrations of paraoxon with a fixed amount of the fusion protein. The reaction velocity increases initially with substrate concentration and gradually levels off. The curves can be fit with the Michaelis-Menten kinetic equation and show very good agreement. This result indicates that the fusion protein follows the same Michaelis-Menten mechanism as that reported for the phosphotriesterase. The mechanism, first developed by Michaelis and Menten in 1913, has been the foundation the greater part of enzyme kinetics. According to the theory, the enzyme first forms a complex with its substrate and this subsequently breaks down giving the free enzyme and the products of the reaction ($E+S=ES \rightarrow E+P$). Under a steady state assumption where the concentration of enzyme-substrate complex remains constant, the reaction velocity can be obtained as:

$$v=V_m[S]/(K_m+[S])$$

where v is the initial velocity, $V_m$ the maximal velocity, S the substrate concentration and $K_m$ the Michaelis constant. At saturating substrate concentrations, when $[S]>>K_m$, $v \approx V_m=k[E]$.

According to the Michaelis-Menten equation, if 1/v is plotted against 1/S, a straight line should be obtained, corresponding to the reciprocal form of the equation:

$$\frac{1}{v} = \frac{1}{V_m} + \frac{K_m}{V_m} \cdot \frac{1}{[S]}$$

Such plot, (Lineweaver-Burk plot) indeed gave linear correlation for the fusion protein and for the recombinant PTE. The kinetic constants were obtained from the plots. The catalytic rate constant (kcat) of the fusion protein was shown to be 66% of the value for PTE. The Km value of the fusion protein is lower than that of the recombinant PTE, suggesting a more favored enzyme-substrate complex formation for the fusion protein than for the enzyme alone. As a result, kcat/Km for the fusion protein is 81% of that of the recombinant enzyme. Since the products of the hydrolysis reaction are both anionic in the reaction buffer at pH 9.0, it is possible that expulsion between the anionic artificial domain and products encouraged leaving of the products from the enzyme active site and therefore shift the equilibrium of the enzyme-substrate complex formation.

The decrease of enzymatic activity in the fusion protein might be due to partial disturbance of protein folding of the enzyme domain by the artificial partner. The sequence of HAP3PEG16 was subjected to computer simulation. The obtained secondary structure of the enzyme domain was compared with crystal structure of the enzyme determined by X-ray diffraction analysis. The computer prediction of the fusion protein showed preservation of five out of eight β strands, mostly in the latter half of the sequence. Most of the α-helical structure of the enzyme domain was disturbed, with only six out of the 14 helices predicted, all at the carboxyl terminus of the enzyme. Detailed study of the secondary structure of the two domains of the fusion protein could be done in the future by circular dichroism and two dimensional NMR.

Nevertheless the absolute value of catalytic constant, kcat, of 2500 s−1 indicated the fusion protein was sufficiently active for catalytic hydrolysis of paraoxon. The pH profile of the fusion protein is similar to that of the recombinant PTE, suggesting that the ionizable group important for activity of the enzyme was not significantly affected by the artificial fusion.

EXAMPLE 5

Immobilization of Fusion Proteins

Given the multiple carboxylate functional groups from the glutamate residues of the artificial domain, the fusion proteins were expected to be selectively adsorbed to cationic surfaces through electrostatic interactions. Computer simulation of HAP3PEG16 showed that the artificial domain contained 11 glutamic acid residues that are entirely accessible to solvents (with reliability >70%); around 70% of glutamic acid residues from the artificial domain were on the outer surface and gave the anionic character of the fusion protein. Computer simulations also showed that the artificial domain is in random coil structure, with the probability of coil more than 80%.

Affinity toward DEAE-Sephadex A-50, an anionic exchange resin, was tested for both HAP3PEG16 and the recombinant phosphotriesterase (PTE). Purified proteins were loaded onto DEAE-Sephadex column and protein was eluted with 50 mM HEPES buffer, pH 8.5 containing different concentrations of sodium chloride. Elution of the fusion and the enzyme was monitored by the enzymatic activity of the eluent. Elution of HAP3PEG required 100 mM NaCl while PTE was found in the first elution fraction, without added salt. These results clearly demonstrate that the fusion protein bound to the cationic surfaces through the anionic artificial domain; the enzyme domain itself showed little binding. The isoelectric point (PI) of the fusion protein is calculated to be 6.02, while that of the recombinant phosphotriesterase is 8.7. At pH 8.5 (where the immobilization was done), the anionic form of fusion protein is dominant; on the other hand, the recombinant enzyme is essentially neutral. The difference of PI values of the fusion protein and the enzyme explains the selective binding of the fusion protein to cationic surfaces.

Other fusion proteins also showed selective adsorption to cationic surfaces. The ionic interaction was probed using whole cell lysates containing fusion proteins with varied number of anionic groups on the artificial domain. The HAP3PEG16 cell lysate showed different affinity with the resin than the pure protein, with most protein eluted at 200 mM NaCl. HAP3EG36 exhibited ion exchange behavior similar to that of HAP3PEG16, although it contained 20 additional glutamic acid residues on the artificial domain. Proteins with same repeating sequence but different chain length, such as HAP4EG18 and HAP4EG28, also didn't seem to show significant differences in binding to DEAE Sephadex. However, with the same number of charges but different number of hydrophobic amino acid residues on the artificial domain, as in the case of HAP3PEG16 and HAP4PEG16, there is a significant difference in ion exchange behavior. HAP4PEG16 showed a bimodal elution at 100 mM and 300 mM NaCl respectively, which is interesting and puzzling. The reason for the bimodal elution is not clear although it is suspected there is a monomer-dimer equilibrium of HAP4PEG16.

A variety of cationic resins functionalized with primary, tertiary and quaternary amino groups were studied for fusion protein immobilization. Both PTE and HAP3PEG16 bind to silica beads and to silica coupled with aminopropyl trimethoxysilane under a variety of pH conditions. The fusion protein was selectively adsorbed on positively charged hydrophilic surfaces through ionic interaction; hydrophilic surfaces without amino functional groups did not adsorb the fusion proteins. Another direct evidence of ionic interaction arises from the observation that fusion proteins were not immobilized on amino surfaces when polyglutamic acid (MW 5000) and polystyrene sulfonate was added to the incubation buffer.

The immobilized HAP on DEAE-Sephadex resin exhibited low catalytic activity for hydrolysis of paraoxon. The relative activity of the immobilized HAP3PEG16 was less than 10% of that of the soluble proteins. Kinetic analysis gave a Km value of 1000 μM for the immobilized enzyme, suggesting a large diffusion effect. Considering that the fusion protein was highly active in solution, a decreased diffusion rate of substrate upon immobilization will significantly lower the apparent enzymatic activity.

The relative activity of immobilized HAP3PEG16 was increased substantially with decrease in resin particle sizes ranging from 0.8 μm to 200 μm in diameter. With Protein-Pak DEAE, a polyacrylate based anionic exchange resin 15 μm in diameter, the relative activity (kcat) of the immobilized fusion protein was 72% compared to the soluble form. The small resin particles provided more surface area in contact with solution and therefore generated less steric hindrance for the diffusion of the substrate from bulk solution to the solid support. The internal diffusion effect was reduced when the protein was immobilized on the outer surface of the resin instead of within the pores. The relative activity of the immobilized HAP3PEG16 on Protein-Pak DEAE was increased with more resin used for immobilization and reached maximum at 3 units per mg of beads, corresponding to approximately monolayer coverage of the fusion protein on the outer surface of the resins. The diameter of the fusion protein is 80 Å, estimated from addition of diameter of the enzyme subunit (50 Å23, 41) and diameter of the artificial domain (30 Å, end to end distance as random coil structure)

A kinetic study of HAP3PEG16 immobilized on Protein-Pak DEAE microspheres was conducted. The Lineweaver-Burk plot indicated that the immobilized fusion protein also followed Michaelis-Menten kinetics. The value of kcat for the immobilized fusion protein was shown to be 1800 s−1, yielding 72% relative activity comparing with the soluble form. The Km of the immobilized protein is 5 times greater than that of the soluble form, attributed to the diffusion hindrance of substrate to the heterogeneous active center upon protein immobilization (compared to the diffusion of substrate to the active site of the soluble enzyme). Another factor for the increase in Km is the affinity of product p-nitrophenolate to the cationic matrix.

While the invention has been described in detail with reference to certain preferred embodiments thereof, it will be understood that modifications and variations are within the spirit and scope of that which is described and claimed.

What is claimed is:

1. A fusion protein comprising:
   (a) a subject protein; and
   (b) a polyanionic domain attached to the subject protein at a terminal region, wherein the polyanionic domain binds to a polycationic coating deposited on a solid support and the polyanionic domain has the formula -[-(SEQ ID NO:1)$_x$-SEQ ID NO:2-]-$_n$ wherein x is 5, 6, 7 or 8 and n is an integer between 1 and 4, and wherein SEQ ID NO:1 is Ala-Gly and SEQ ID NO:2 is Pro-Glu-Gly, wherein the terminal region is the amino-terminal region.

2. A fusion protein comprising:
   (a) a subject protein; and
   (b) a polyanionic domain attached to the subject protein at a terminal region, wherein the polyanionic domain binds to a polycationic coating deposited on a solid support and the polyanionic domain has the formula -[-(SEQ ID NO:1)$_x$-SEQ ID NO:2-]-$_n$ wherein x is 5, 6, 7 or 8 and n is an integer between 1 and 4, and wherein SEQ ID NO:1 is Ala-Gly and SEQ ID NO:2 is Pro-Glu-Gly, wherein the terminal region is the carboxyl-terminal region.

3. The protein of claim 1, wherein the polyanionic domain contains 10 to 30 anionic amino acid residues.

4. The protein of claim 1, wherein x is 5.

5. The protein of claim 1, wherein x is 6.

6. A fusion protein comprising:
   (a) a subject protein; and
   (b) a polyanionic domain attached to the subject protein at a terminal region, wherein the polyanionic domain binds to a polycationic coating deposited on a solid support and the polyanionic domain has the formula -[-(SEQ ID NO:1)$_x$-SEQ ID NO:7-]-$_n$ or -[-(SEQ ID NO:1)$_y$-SEQ ID NO:8-]-$_m$, wherein x or y is 0, 1, 2, 3, 4, 5, 6, 7 or 8 and n or m is an integer between 1 and 40, and wherein SEQ ID NO:1 is Ala-Gly, SEQ ID NO:7 is Pro-Asp-Gly and SEQ ID NO:8 is Asp-Gly, wherein the terminal region is the amino-terminal region, wherein the polyanionic domain contains 10 to 30 anionic amino acid residues.

7. A fusion protein comprising:
   (a) a subject protein; and
   (b) a polyanionic domain attached to the subject protein at a terminal region, wherein the polyanionic domain binds to a polycationic coating deposited on a solid support and the polyanionic domain has the formula -[-(SEQ ID NO:1)$_x$-SEQ ID NO:7-]-$_n$ or -[-(SEQ ID NO:1)$_y$-SEQ ID NO:8-]-$_m$, wherein x or y is 0, 1, 2, 3, 4, 5, 6, 7 or 8 and n or m is an integer between 1 and 40, and wherein SEQ ID NO:1 is Ala-Gly, SEQ ID NO:7 is Pro-Asp-Gly and SEQ ID NO:8 is Asp-Gly, wherein the terminal region is the carboxyl-terminal region, wherein the polyanionic domain contains 10 to 30 anionic amino acid residues.

8. A fusion protein comprising:
   (a) a subject protein; and
   (b) a polyanionic domain attached to the subject protein at a terminal region, wherein the polyanionic domain binds to a polycationic coating deposited on a solid support and the polyanionic domain has the formula -[-(SEQ ID NO:1)$_y$-SEQ ID NO:6-]-$_m$, wherein y is 0, 1, 2, 3, 4, 5, 6, 7 or 8 and m is an integer between 1 and 40, and wherein SEQ ID NO:1 is Ala-Gly and SEQ ID NO:6 is Glu-Gly, wherein the polyanionic domain contains 10 to 30 anionic amino acid residues.

9. A solution comprising a plurality of fusion proteins of any one of claims 1, 2, 6, 7 or 8.

* * * * *

SEQUENCE LISTING

```
<160> NUMBER OF SEQ ID NOS: 9

<210> SEQ ID NO 1
<211> LENGTH: 2
<212> TYPE: PRT
<213> ORGANISM: Artificial sequence
<220> FEATURE:
<223> OTHER INFORMATION: Synthetic construct

<400> SEQUENCE: 1

Ala Gly
1

<210> SEQ ID NO 2
<211> LENGTH: 3
<212> TYPE: PRT
<213> ORGANISM: Artificial sequence
<220> FEATURE:
<223> OTHER INFORMATION: Synthetic construct

<400> SEQUENCE: 2

Pro Glu Gly
1

<210> SEQ ID NO 3
```

```
<211> LENGTH: 5
<212> TYPE: PRT
<213> ORGANISM: Artificial sequence
<220> FEATURE:
<223> OTHER INFORMATION: Synthetic construct: 5 lac Z segment

<400> SEQUENCE: 3

Met Ile Thr Asn Ser
1               5

<210> SEQ ID NO 4
<211> LENGTH: 21
<212> TYPE: DNA
<213> ORGANISM: Artificial sequence
<220> FEATURE:
<223> OTHER INFORMATION: Synthetic construct: Linker

<400> SEQUENCE: 4
gatccccggg taccgagctc g                                         21

<210> SEQ ID NO 5
<211> LENGTH: 21
<212> TYPE: DNA
<213> ORGANISM: Artificial sequence
<220> FEATURE:
<223> OTHER INFORMATION: Synthetic construct: Linker

<400> SEQUENCE: 5
aattcgagct cggtacccgg g                                         21

<210> SEQ ID NO 6
<211> LENGTH: 2
<212> TYPE: PRT
<213> ORGANISM: Artificial sequence
<220> FEATURE:
<223> OTHER INFORMATION: Synthetic construct

<400> SEQUENCE: 6

Glu Gly
1

<210> SEQ ID NO 7
<211> LENGTH: 3
<212> TYPE: PRT
<213> ORGANISM: Artificial sequence
<220> FEATURE:
<223> OTHER INFORMATION: Synthetic construct

<400> SEQUENCE: 7

Pro Asp Gly
1

<210> SEQ ID NO 8
<211> LENGTH: 2
<212> TYPE: PRT
<213> ORGANISM: Artificial sequence
<220> FEATURE:
<223> OTHER INFORMATION: Synthetic construct

<400> SEQUENCE: 8

Asp Gly
1

<210> SEQ ID NO 9
<211> LENGTH: 3
<212> TYPE: PRT
<213> ORGANISM: Artificial sequence
```

-continued

```
<220> FEATURE:
<223> OTHER INFORMATION: Synthetic construct

<400> SEQUENCE: 9

Gly Asp Arg
1
```